United States Patent [19]

Fujii et al.

[11] 4,030,977

[45] June 21, 1977

[54] METHOD FOR PURIFICATION OF PHYSIOLOGICALLY ACTIVE SUBSTANCE USING ENZYME-ENZYME INHIBITOR SYSTEM

[75] Inventors: Setsuro Fujii, Tokushima; Yasumichi Kajita, Kyoto; Seizi Hiraku, Takatsuki; Heizo Kira, Ibaragi; Hideki Aishita, Takatsuki; Keiko Muryobayashi, Ibaragi; Hiroshi Terashima, Takatsuki; Akira Akimoto, Osaka; Ken Taniguchi, Higashinose; Minoru Wada, Kishiwada, all of Japan

[73] Assignee: Ono Pharmaceutical Co., Ltd., Osaka, Japan

[22] Filed: Mar. 19, 1976

[21] Appl. No.: 668,378

Related U.S. Application Data

[63] Continuation-in-part of Ser. No. 426,143, Dec. 19, 1973, abandoned.

[30] Foreign Application Priority Data

Dec. 19, 1972 Japan .......................... 47-127396

[52] U.S. Cl. .............................. 195/66 R; 195/68; 195/DIG. 11

[51] Int. Cl.² ........................ C12D 13/10

[58] Field of Search ......... 195/63, 66, 68, DIG. 11, 195/2, 4, 104, 115, 116; 260/112 R

[56] References Cited

FOREIGN PATENTS OR APPLICATIONS 2,363,201  12/1972  Germany .................... 195/66 R

OTHER PUBLICATIONS

Cuatrecasas, "Protein Purification by Affinity Chromatography," J. Biological Chem., June 25 (1970) pp. 3059–3065.
Feinstein, "Affinity Chromatography of Biological Macromolecules," Naturwissenschaften, vol. 8 (1971), pp. 389–396.

*Primary Examiner*—R. B. Penland
*Attorney, Agent, or Firm*—Sughrue, Rothwell, Mion, Zinn & Macpeak

[57] ABSTRACT

A method for isolating and purifying a physiologically active substance contained in a tissue or a body fluid using an insoluble type naturally occurring proteolytic enzyme inhibitor or an insoluble type proteolytic enzyme alone or in combination with the insoluble type naturally occurring proteolytic enzyme inhibitor is disclosed.

4 Claims, No Drawings

METHOD FOR PURIFICATION OF PHYSIOLOGICALLY ACTIVE SUBSTANCE USING ENZYME-ENZYME INHIBITOR SYSTEM

CROSS-REFERENCE TO RELATED APPLICATION

This application is a continuation-in-part application of Ser. No. 426,143 filed Dec. 19, 1973 now abandoned.

BACKGROUND OF THE INVENTION

This invention relates to a method for isolating and purifying a physiologically active substance contained in a living organism.

Enzymes, such as trypsin, kallikrein, plasmin, chymotrypsin and the like, which take part in the kinin production and consumption in a living organism play an important role in regulating the circulatory system and the inhibitors against such enzymes derived from the blood and organ origins also play an important role in the maintenance of the normal functioning of the living body together with these enzymes in cooperation.

SUMMARY OF THE INVENTION

An object of the present invention is to provide a method for isolating and purifying enzymes which take part in the production and consumption of kinin, and their naturally occurring inhibitors using an isoluble enzyme-enzyme inhibitor system or an enzyme-insoluble enzyme inhibitor system, which method comprises either converting the enzymes into an insoluble type, specifically combining the corresponding enzyme inhibitors and releasing of the inhibitors using an eluent having a specific composition, or converting the inhibitors into an insoluble type, specifically combining the corresponding enzymes and releasing of the enzymes using an eluent having a specific composition. Depending upon the purpose, it is also possible to simultaneously obtain the related enzyme and its inhibitor from organs or body fluids if a series of the above treatments is carried out in parallel using a combination of an insoluble type of the enzyme and the corresponding enzyme inhibitor.

DETAILED DESCRIPTION OF THE INVENTION

The source material which can practically be used in the present invention includes organs such as the heart, lung, pancreas, parotid, kidney, liver, spleen, etc. of mammals, for example, a horse, bovine, swine, dog, rabbit, sheep, guinea pig, rat and the like and body fluids such as blood, lymph, urine and the like of humans and the mammals enumerated above.

The term "proteolytic enzyme" used herein includes an enzyme which is capable of producing kinin from kininogen, i.e., trypsin, kallikrein or plasmin, an enzyme which is capable of consuming kinin, i.e., chymotrypsin, and an enzyme which can be inhibited by an inhibitor capable of inhibiting the above enzymes, i.e., thrombin. The term "naturally occurring proteolytic enzyme inhibitor" used herein means an inhibitor which is proteinous in nature and is capable of reversibly inhibiting the activity of the above-described enzyme.

The term "physiologically active substance" used herein includes both proteolytic enzymes which take part in the production-consumption of kinin and an inhibitor which is proteinous in nature and inhibits the activity of the above proteolytic enzyme.

Examples of naturally occurring proteolytic enzyme inhibitors of an insoluble type which can be used for the separation according to the method of this invention are well-known inhibitors such as Kunitz's inhibitor or organ origin [M. Kunitz & J. H. Northrop; *J. Gen. Physiol.*, 19, 991, (1936)]; Kazal's inhibitor of organ origin [L. A. Kazal, D. S. Spicer & R. A. Brabinsky; *J. Am. Chem. Soc.*, 70, 3034, (1948)]; an $\alpha_1$-globulin inhibitor of blood origin [H. Fritz; *Z. Phys. Chem.*, 350, 933, (1969)]; an $\alpha_2$-globulin inhibitor of blood origin [M. Laskouski; *J. Biol, Chem.*, 204, 153, (1953)]; an inhibitor of ovomucoid in egg white [R. E. Feeney; *J. Biol. Chem.*, 244, 1957, (1969)]; and other inhibitors of vegetable origin, e.g., enzyme inhibitors in soybean, potato (Japanese Patent Publication No. 27833/1971), corn [K. Hochstasser, K. Illchmann & E. Werle; *Z. Physiol. Chem.* (Hoppe-Seylers), 351, 721, (1970)]; or inhibitors of microorganism origin, e.g., those produced from *Streptomyces roseus* [H. Umezawa; *J. Antibiotics.*, 22, 283, (1969)], or the inhibitors obtained in the present invention.

These inhibitors can be chemically coupled to insoluble carriers which are inactive, porous and also hydrophilic, such as agarose, dextran, polyacrylamides and the like. Sepharose (a trade mark manufactured by Pharmacia Fine Chemical Co., Ltd.), Sephadex (a trade mark manufactured by Pharmacia Fine Chemical Co., Ltd.) and Biogel (a trade mark manufactured by Bio-rad Laboratories Co., Ltd.) can be used as the agarose, dextran and polyacrylamide, respectively.

When a polysaccharide such as agarose or dextran is employed as an insoluble carrier to which a naturally occurring proteolytic enzyme inhibitor is chemically bound, the polysaccharide is first activated with cyanogen bromide, [e.g., as described in Rolf Axen, Jerker Porath & Sverker Ernback, Nature, 214, 1302–1304 (1967)]. For example, 15 to 20g of cyanogen bromide and 100ml of water are added to 100ml of agarose, and 8N NaOH is added dropwise to the resulting mixture over about 15 minutes with stirring under ice-cooling while maintaining the pH at 10.5 to 11.5 and a temperature of 10° to 15° C, whereby the hydroxy groups of the agarose are converted into an active iminocarbonate group

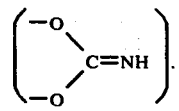

The resulting reaction mixture is then washed rapidly with about 1l of a 0.1M aqueous sodium bicarbonate solution on a glass filter and added to a mixture of 1g of a protein and 100ml of a 0.1M aqueous sodium bicarbonate solution. The resulting mixture is then allowed to react for 3 hours at room temperature and then overnight at 4° C. In this procedure, an amino group of the protein used in directly bound to the agarose by an iminocarbonate ester, carbamic acid ester or pseudourea linkage.

Alternatively, 100 ml of the agarose activated as described above is added to 100ml of a 2M solution of an ω-diamine compound such as ethylene diamine which has been adjusted to a pH of 10 with 6N hydrochloric acid and the mixture is allowed to react overnight at 4° C to produce aminoethyl-agarose. 1g of a protein and 100ml of water are added to the above reaction followed by pH adjustment to 4.7. 2.7g of 1-ethyl-3-(3-dimethylaminopropyl) carbodiimide (a water-soluble carbodiimide, hereinafter referred to as "WSC") is then added thereto and the mixture is allowed to react overnight at 4° C. In this procedure, a carboxyl group of the protein is dehydrated-condensed with an amino group whereby the protein is bound to the agarose through an ethylamino group.

In the same manner, 100ml of a 2M solution of an ω-aminocarboxylic acid such as ε-aminocaproic acid is added to 100ml of the agarose activated as described above and the mixture is allowed to react overnight at 4° C at a pH of 8 to 10 to produce carboxyalkyl agarose. 1g of a protein and 100ml of water are then added to the above carboxyalkyl agarose and, after adjusting the pH of the mixture to 4.7, 2.5g of WSC is added thereto followed by allowing the mixture to react overnight at 4° C. In this procedure, an amino group of the protein is dehydrated-condensed with a carboxylic acid whereby the protein is bound to agarose through a carbonylhexyl group.

In a further embodiment for binding the protein to agarose, 5 mmole of bromoacetic acid and 6 mmole of N-hydroxysuccinimide are dissolved in 40ml of dioxane, and 6 mmole of dicyclohexylcarbodiimide (DCC) is added thereto followed by allowing the mixture to react for 2 hours. The DCC-urea thus obtained is removed by filtration, and the filtrate is reacted with 100ml of amino-ethyl-agarose at 4° C and pH 7.5. After reaction for one hour, the reaction mixture is washed with cold 0.1M aqueous NaCl solution to provide bromoacetyl-agarose. 1g of a protein is dissolved in 0.1M acetate buffer (pH 5.1) and 100ml of the bromoacetyl-agarose obtained above followed by reacting overnight at 4° C. The reaction mixture is washed with a 0.1M aqueous sodium bicarbonate solution on a glass filter and suspended in 100ml of the same aqueous sodium bicarbonate. The suspension is then allowed to react for 3 hours at room temperature followed by allowing it to stand overnight at 4° C whereby the protein is bound to the gel through an amino group, tyrosine and histidine of the protein.

Also, a protein can be bound to agarose using aminoethyl-agarose by the following procedure. For example, 100ml of water and 10g of succinic anhydride are added to 100ml of aminoethyl-agarose and 20% aqueous NaOH is added dropwise thereto to adjust the pH to 6.0. After the pH stabilizes, the mixture is allowed to stand overnight to obtain succinylaminoethyl-agarose. A mixture of 100ml of the solution obtained above and a protein (1g/100ml) is adjusted to a pH of 4.7, and 2.5g of WSC is added to the mixture followed by allowing the mixture to react overnight at 4° C whereby the protein is bound to the succinylamino-ethyl-agarose through an amino group. Alternatively, 10ml of amino-ethyl-agarose is added to 10ml of a 0.2M sodium borate (pH 9.0) containing 40% dimethylformamide (DMF), and the mixture is reacted with 30mg of p-nitrobenzoyl azide at room temperature for one hour. The reaction mixture is washed with 50% DMF, and is reduced with 400 mg of sodium hypothionate at a pH of 8.5 at 50° C for 40 minutes to produce p-aminobenzamidoethyl-agarose, The product thus obtained is then diazotized with a 0.1M sodium nitrite in 0.5N HCl at 0° C for 5 minutes. The mixture is washed with 0.2M NaCl and immediately reacted with a protein (100mg/10ml of water) at 0° C for 2 hours while keeping the pH of the mixture at 8.5 with 1N NaOH whereby the protein is bound to the agarose through tyrosine and histidine of the protein.

In case of using a polyacrylamide as an insoluble carrier, 1g of Biogel P-300, a typical example of suitable polyacrylamides, is reacted with 15 to 20ml of ethylenediamine at a temperature of 90° C for 8 hours. After allowing the mixture to cool, it is washed with a cold aqueous sodium chloride solution on a glass filter to obtain aminoethyl-Biogel P-300. A mixture consisting of 100ml of the thus obtained swelled Biogel P-300, 1g of a protein, 100ml of water and 2.5g of WSC is then reacted overnight at a temperature of 4° C at pH of 4.7 whereby the protein is bound to the Biogel through a carboxyl group of the protein. Alternatively, Biogel P-300 is swelled with water and hydrated hydrazine is added thereto in an amount sufficient to provide a concentration of 3M hydrazine followed by allowing the mixture to react at 50° C for 8 hours with stirring. 1g of the resulting Biogel P-300 is then suspended in 150ml of 0.3N HCl and the mixture is cooled to 4° C. 10ml of 1M sodium nitrite is added thereto and, after 30 minutes' reaction, the reaction mixture is washed rapidly with 0.3N HCl, 0.1M sulfamic acid and cold water, successively, and added to 1g of a protein dissolved in 100ml of a 0.1M sodium borate. The mixture is then allowed to react at 0° C for 1.5 hours and thereafter reacted with 20ml of 1M ammonia and 20ml of 1M ammonium chloride for 2 hours. The reaction mixture is finally washed with 0.2M NaCl whereby the protein is bound to the gel through an amino group of the protein. In a similar manner, 1g of the hydrazide gel is suspended in 300 ml of 0.1M NaCl and succinic anhydride is added gradually to the suspension with stirring while keeping a pH of the resulting mixture at 4 with 2N NaOH followed by allowing the mixture to react for 2 hours. After washing with cold water, 300mg of a protein and 800mg of WSC are added thereto and the mixture is allowed to react overnight at a temperature of 4° C and a pH of 4.7 whereby the protein is bound to the gel through an amino group of the protein.

The proteolytic enzyme of an insoluble type which can practically be used for the separation in the present invention includes trypsin, chymotrypsin, kallikrein, plasmin, thrombin and the like.

These enzymes can be chemically bound to the above described insoluble carriers such as agarose, dextran and polyarylamide in the same manner as in the case where naturally occurring proteolytic enzyme inhibitors are bound to the insoluble carriers.

Since these enzymes and enzyme inhibitors of the insoluble type are capable of specifically adsorbing the corresponding enzyme inhibitors and enzymes, respectively, they can be used for separating and purifying the desired substances of the present invention by mixing and stirring the insolubilized enzymes and/or the insolubilized enzyme inhibitor with an organ extract solution or a diluted solution of blood, lymph or a body fluid.

In the method of this invention, various procedures such as the extraction of the physiologically active substances from various organs, the dilution of blood, lymph of body fluid, and the binding of physiologically active substances contained in the extract or the diluted blood, lymph or body fluid to the insoluble enzyme or to the insoluble inhibitor, and the washing of the resulting coupled material can be carried out at a pH in the range of 4 to 10 using an aqueous buffer solution having an ionic strength in the range of 0 to 5, for example, a triethanolamine-hydrochloric acid buffer, a trisaminomethane-hydrochloric acid buffer, a boric acid-potassium chloride-sodium hydroxide buffer, an acetic acid-sodium acetate buffer, a potassium phosphate-sodium phosphate buffer or water and the like at a temperature in the range of 0° to 30° C.

Likewise, the release of the physiologically active substances which have been bound to the insoluble enzyme or the insoluble enzyme inhibitor can be carried out at a pH in the range of 0.5 to 6 using an aqueous buffer solution, for example, dilute hydrochloric acid, acetic acid, an acetic acid-sodium acetate buffer, a hydrochloric acid-potassium chloride buffer, a potassium phosphate-sodium phosphate buffer, a potassium citrate-sodium hydroxide buffer and the like at a temperature in the range of 0° to 30° C.

In extracting physiologically active substances from the organs, the organ is first minced by an appropriate means such as Waring blender and the like into a size sufficient to homogenize it, and the aqueous buffer solution for extraction enumerated above is added to the minced organ, followed by homogenization. The aqueous phase containing the physiologically active substances is then separated from the minced organ by centrifuging or filtration to obtain an extract of the physiologically active substances. When the physiologically active substances are contained in a blood plasma of the raw blood, it is necessary to subject the raw blood to centrifuging in order to remove the blood cells. The blood plasma thus obtained as well as other body fluids can be diluted, if necessary, with the above aqueous buffer solution to ensure a suitable contact with and adsorption on an insoluble enzyme or an insoluble enzyme inhibitor, i.e., by reducing the viscosity of the blood plasma and body fluids and adjusting the pH thereof.

In the above procedure, the entire procedure is preferably carried out at a temperature ranging from 0° to 4° C if the desired physiologically active substances are considered to be thermally unstable.

As described above, the separation and purification of the desired substances can be by contacting the insolubilized enzyme and/or the insolubilized enzyme inhibitor by mixing and stirring the insolubilized enzyme and/or enzyme inhibitor with this solution or by passing this solution through a column packed with an enzyme or an enzyme inhibitor of the insoluble type to adsorb the desired substances, washing the insoluble carrier having the corresponding substances adsorbed thereon, eluting the substances therefrom using an appropriate buffer and the like as an eluant. When enzymes are eluted and purified, the desired substances in the eluate can be detected by determining the enzymatic activities of the enzymes thus obtained, for example, esterase activity using an acetyl-tyrosine ethyl ester as a substrate, casein decomposition activity, kinin production activity and the like. When enzyme inhibitors are eluted and purified, their activities can be detected by determining the degree of inhibition against the enzymatic activities of the corresponding enzymes. In column chromatography, the adsorption can be carried out at a maximum flow rate, for example, 50 ml/hour/bottom area $cm^2$ in case of using Sepharose 4B as a carrier, without effecting the adsorbability. The adsorption can also be effected in a batchwise procedure without using a column. In either case, the adsorption and the elution of an insoluble enzyme or an insoluble enzyme inhibitor can be conducted by a well established techniques using ion-exchange resin which is apparent to one skilled in the art. Generally, column chromatography is preferred when it is desired to obtain an eluate containing the desired product in a high concentration and when two or more substances having affinity constants which are close to each other are fractionally eluted.

The amount of the physiologically active substances to be adsorbed varies with the amount of an insoluble enzyme or an insoluble enzyme inhibitor coupled to the carrier and with a pH value. For example, 10 mg of a soybean trypsin inhibitor can easily be coupled to 1 ml of Sepharose 4B which has previously been activated with cyanogen bromide, and about 8 mg of trypsin can be adsorbed on 1 ml of the above obtained soybean trypsin inhibitor-Sepharose 4B at a pH of 7 to 8, but at a pH below 1 an appreciable amount of trypsin cannot be adsorbed on the soybean trypsin inhibitor-Sepharose.

If desired, enzymes and inhibitors each bound to the insoluble carrier can be employed in parallel where proteolytic enzymes and their inhibitors concomitantly present in organs or body fluids can simultaneously be separated and purified. Therefore, the operation according to the present invention can conveniently be carried out in a short period of time. That is, the starting solution containing the enzyme and the enzyme inhibitor first adsorbs the corresponding enzyme using the insoluble enzyme inhibitor and then adsorbs the corresponding enzyme inhibitor using the insoluble enzyme whereafter the enzyme and the inhibitor contained in the solution can be separated and purified by separately eluting the enzyme and the inhibitor.

The solution containing the released physiologically active substances thus obtained can then be purified and concentrated in the manner commonly employed in the purification and concentration of physiologically active substances. For example, the solution can be concentrated using an evaporator, desalted and concentrated using a molecular sieving membrane, for example, a cellulose acetate membrane, a polyelectrolyte complex membrane and the like, or freeze-dried to obtain a product which can be employed as a pharmaceutical preparation.

Since the method of the present invention utilizes the affinity between a high molecular weight proteolytic enzyme and a high molecular weight proteolytic enzyme inhibitor, a specific and very strong binding occurs only between the complementary high molecular weight molecules which is critically restricted in terms of the stereochemistry as compared with a mere ionic binding thereby increasing the degree of purification, which is in no way comparable to purification methods using ion-exchange resins. Thus, the method of this invention provides a great advantage in obtaining physiologically active substances over the purification methods of the prior art employed for such a purpose. In addition, the proteolytic enzymes and proteolytic enzyme inhibitors bound to insoluble carriers exhibit not only a specific binding property but also an excellent stability which enables them to be repeatedly used semi-permanently without complicated regeneration treatments. Therefore, the method of the present invention is believed to have a wide variety of utilities for treating physiologically active substances in large quantities on an industrial scale.

Further, the present inventors did not find any appreciable increase in viscosity or a remarkable decrease in the flow rate of the high molecular weight substances when combined with a starch gel or ion-exchange resins, which is often observed in the conventional methods.

The methods of the present invention makes it possible to isolate and purify the physiologically active substances present in a living organism, for example, kallikrein, plasmin, thrombin, trypsin, chymotrypsin, kallikrein inhibitor or trypsin inhibitor, in a single treatment contrary to the conventional method for isolating and purifying these substances where a number of complicated separation procedures are required, for example, an ammonium sulfate fractionation, precipitation with a solvent followed by separation, column chromatography, gel filtration and the like [as disclosed, for example in, B. Kassell, M. Radicevic, S. Berlow, R. J. Peanasky & M. Laskowski, Sr., *J. Biol. Chem.*, 238, 3274-3279 (1963) and H. Moriya, A. Kato & H. Fukushima, *Biochem. Pharmacol.*, 18 (2), 549-552 (1969)]. Further, the present invention makes it possible to produce these substances in high purity at low cost and would facilitate development of various utilizations of organs and body fluids of stock animal sources and their waste materials.

Furthermore, the present invention makes it possible to improve the production of useful pharmaceuticals because these physiologically active substances present in a living organism are known to be useful therapeutics as circulatory hormones [as disclosed in K. M. Herrligkoffer, *Med. Wsch.*, 6, 353 (1952)] or agents for treating or alleviating thrombus [J. L. Ambrus, C. M. Ambrus, J. E. Sokal, G. Markus, N. Back, L. Stutzman, R. Razis, C. A. Ross, B. H. Smith, A. C. Rekate, G. L. Collins, D. L. Kline & J. B. Fishman, *Am. J. Cardiol.*, 6, 462 (1960)] or flammatory disease associated with acute pain such a pancreatitis [as disclosed in E. K. Frey, *Therapiewoche*, 4, 323 (1953/54) and E. Weke, K, Tauber, W. Hartenback & M. M. Forell, *Münch. Med. Wschr.*, 100, 1265 (1958)] and the like.

The present invention will further be illustrated with reference to the following examples, but these examples are not to be construed as limiting the scope of this invention. In the examples, all percentages are by weight.

EXAMPLE 1

Purification of Trypsin from Bovine Lung

To 1 Kg of bovine lung which had been frozen and cut into pieces was added 1 l of a 0.1M triethanolamine buffer (containing 0.3M sodium chloride and 0.01M calcium chloride, pH 7.8). The resulting mixture was ice-cooled and then homogenized using a Waring blender for 10 minutes. The homogenate was stirred for an additional one hour and 100 g of Celite 545 (a diatomaceous silica product, a trade mark manufactured by Johns-Manville Products Corp.) was added thereto. The resulting suspension was centrifuged. The precipitate was suspended in the same volume of the above described buffer and centrifuged again. To the combined supernatant solution was added 50% trichloroacetic acid to a final concentration of 2.5%, and the resulting solution was allowed to stand for 30 minutes and then centrifuged. The supernatant solution was adjusted to a pH of 7.8 with 3.5N sodium hydroxide and filtered to obtain 1950 ml of a yellow transparent solution containing a physiologically active substance.

On the other hand, 1 g of trypsin was reacted overnight at a pH of 9.2 with 100 ml of Sepharose 4B (a trade mark manufactured by Pharmacia Fine Chemical Co., Ltd.) which had previously been activated with 10 g of cyanogen bromide, to form trypsin-Sepharose 4B (insoluble enzyme). 75 ml of the trypsin-Sepharose 4B was transferred to a column (2.2 × 20 cm), and 1950 ml of the above obtained solution (1,053,000 trypsin-kallikrein inhibitor units) was applied to the column. The column was washed with a 0.1M triethanolamine buffer (pH 7.8) until the elluent was entirely protein-free. The column was then eluted with 0.25M KCl—HCl (pH 1.8) to obtain bovine lung trypsin inhibitor in a yield of 80%. The inhibitor thus obtained was found to have a specific activity increased to 53 to 130 times compared with the solution as initially applied. The product thus obtained was subsequently desalted by passing it through a column of Sephadex G-25 (a trade mark manufactured by Pharmacia Fine Chemical Co., Ltd.).

EXAMPLE 2

Purification of Kallikrein From Swine Serum

To 5 ml of Sepharose 4B were added to 5 ml water and 1 g of cyanogen bromide and the reaction was conducted for a period of 10 minutes while maintaining a pH in a range of from 10.5 to 12.0 with 1N sodium hydroxide. The reaction mixture was washed with 200 ml of cold water, and 5 ml of the solution of the bovine lung trypsin inhibitor obtained as described in Example 1 (a 0.1M borate buffer, pH 9.2) was added thereto. The reaction mixture was adjusted to a pH of 9.2 with 1N sodium hydroxide and then the reaction was effected at a temperature of 4° C for 17 hours. 4 ml of the thus obtained bovine lung trypsin inhibitor-Sepharose 4B was transferred to a column and equilibrated with 20 ml of 0.1M trisaminomethane-hydrochloric acid-0.5M sodium chloride (pH 8.5), and an ammonium sulfate fraction of globulin from swine serum ($OD_{280}$ = 89.82) was added thereto. The column was washed with the above buffer, and then eluted with either 0.1M acetic acid or 0.01N hydrochloric acid. The eluate was added drop-wise to a 2M Tris-HCl buffer (pH 8.5). It was observed that the resulting fractions were purified about 43 times with a yield of activity being about 83%.

EXAMPLE 3

A serum globulin fraction was treated following the procedures as described in Example 1 and then Example 2 using the system comprising a combination of the trypsin-Sepharose 4B as used in Example 1 and the trypsin inhibitor-Sepharose 4B used in Example 2 to fractionally obtain trypsin-kallikrein inhibitor and kallikrein in a continuous manner.

EXAMPLE 4

Fractionation of Pancreas Proteolytic Enzyme

A mixture of 1 g of pancreas powder and 50 ml of cold water was stirred for a period of 45 minutes, and adjusted to a pH of 4.1 with 2M acetic acid. The mixture was further stirred for an additional 1.5 hours, followed by centrifuging to obtain 48 ml of the supernatant. A 2 ml portion of the resulting supernatant was diluted with 10 ml of a 0.1M trisaminomethane-hydrochloric acid buffer, pH 8.0 (containing 10 mM $CaCl_2$)

and the solution was applied to a 4 ml column packed with bovine lung trypsin inhibitor-Sepharose 4B which had previously been equilibrated with the same buffer as used above. The unabsorbed substance showing an absorption at a wavelength of 280 mμ was washed out, and the column was then eluted successively with a 0.1M acetate buffer (pH 4.0), a 0.1N acetic acid and a 0.02M hydrochloric acid to fractionally obtain chymotrypsin, kallikrein and trypsin, respectively.

EXAMPLE 5

Isolation of Kallikrein-Like Substance From Human Urine

In the same manner as described in Example 2, urine from a subject was treated using the trypsin inhibitor-Sepharose 4B used in Example 2. The resulting substance having a hypotensive activity showed a degree of purification of 10 times.

EXAMPLE 6

Purification of Kallikrein From Swine Pancreas 10 g of swine pancreas powder was suspended in 500 ml of cold water and adjusted to a pH of 4.1 with 2M acetic acid. The mixture was stirred for 1 hour while being cold, followed by centrifuging to obtain supernatant, which was then adjusted to a pH of 8.0 with 8N NaOH to form precipitates. The precipitates were removed from the supernatant by centrifuging to obtain 460 ml of clear extract solution.

The solution was applied to an affinity chromatography using joined columns comprising a column packed with 20 ml of soybean trypsin inhibitor-Sepharose 4B and a column packed with 5 ml of bovine lung trypsin inhibitor-Sepharose 4B, wherein the former column was positioned upstream, both columns being equilibrated with 0.1M Tris-HCl buffer (pH 8.0) beforehand.

After charging was completed, the columns were washed with the starting buffer (0.1M Tris-HCl, pH 8.0) and then they were disjoined into two separate columns.

The column packed with bovine lung trypsin inhibitor-Sepharose 4B was successively eluted with 100 ml of a 0.1M acetate buffer (pH 4.0) and 100 ml of a 0.1N acetic acid (pH 2.7) to fractionally obtain kallikrein. Upon eluting, the eluate was dripped into 11 ml of a 2M Tris-HCl buffer (pH 8.5) to obtain kallikrein under a stable condition.

The thus obtained solution containing kallikrein had specific activity about 200 times as high as that of the starting solution and was so pure that when applied to disk electrophoresis it gave two bands, i.e., kallikreins A and B. The yield was about 70% by weight.

Then the column packed with soybean trypsin inhibitor-Sepharose 4B and column packed with bovine lung trypsin inhibitor-Sepharose 4B were eluted with a 0.1N HCl to remove trypsin and chymotrypsin and other impurities.

Tris-HCl stands for trisaminomethane-hdyrochloric acid.

While the present invention had been described in greater detail with reference to the specific embodiments, it will be apparent to one skilled in the art that various changes and modifications can be made therein without departing from the spirit and the scope of the present invention.

What is claimed is:

1. A method for isolating and purifying kallikrein contained in mammalian tissue or body fluid which comprises contacting an extract of said tissue or said body fluid with a material formed of an insoluble carrier chemically coupled to a proteolytic enzyme inhibitor for kallekrein, said material being selected from an insolubilized naturally occurring enzyme inhibitor so as to bind said kallikrein and eluting said kallikrein therefrom using first 0.1 M acetate buffer of pH 4.0 and second 0.1 N acetic acid solution and immediately adding the eluate drop-wise to 2M Tris-amino-methane HCl buffer of pH 8.0 to 10.0, wherein said process is carried out by contacting said extract of said tissue or said body fluid with insoluble carrier chemically coupled to soybean trypsin inhibitor and then with insoluble carrier chemically coupled to bovine lung trypsin inhibitor.

2. The method of claim 1 wherein said insoluble carrier and enzyme inhibitor are bonded through an iminocarbonate ester group, a carbamic acid ester group, a pseudourea linkage, an alkyl amino group, a carbonyl alkyl group, an amino group, the tyrosine moiety of protein, the histidine of protein or a carboxyl group.

3. The method of claim 1 wherein said insolubilized enzyme inhibitor comprises said enzyme inhibitor chemically bound to an insoluble agarose, dextran or polyacrylamide carrier.

4. The method of claim 1 including concentrating said kallikrein and recovering said kallikrein.

* * * * *